United States Patent [19]

Goldberg et al.

[11] Patent Number: 5,095,027
[45] Date of Patent: Mar. 10, 1992

[54] METHOD FOR TREATING REPERFUSION INJURY EMPLOYING L-2-OXOTHIAZOLIDINE-4-CARBOXYLIC ACID

[75] Inventors: Dennis I. Goldberg, Palatine; David C. Madsen, Libertyville; W. Bruce Rowe, Evanston, all of Ill.

[73] Assignee: Clintec Nutrition Co., Deerfield, Ill.

[21] Appl. No.: 662,557

[22] Filed: Feb. 28, 1991

[51] Int. Cl.⁵ .......................................... A61K 31/425
[52] U.S. Cl. ................................................ 514/369
[58] Field of Search ............................. 514/547, 369

[56] References Cited

U.S. PATENT DOCUMENTS 4,647,571  3/1987  Meister et al. ....................... 514/369
4,665,082  5/1987  Meister et al. ....................... 514/365

FOREIGN PATENT DOCUMENTS 0257992  3/1988  European Pat. Off. .
0318330  3/1988  European Pat. Off. .

Primary Examiner—Frederick E. Waddell
Assistant Examiner—Diane Gardner
Attorney, Agent, or Firm—Hill, Van Santen, Steadman & Simpson

[57] ABSTRACT

The present invention provides a method for treating and/or reducing ischemic reperfusion injury. To this end, in embodiment, a method for treating and/or reducing reperfusion injury is provided comprising the step of administering to a patient in danger of reperfusion injury a therapeutically effective amount of L-2-oxothiazolidine-4-carboxylic acid. In an embodiment, a method is provided for limiting an expected ischemic reperfusion injury comprising the step of administering prior to an expected ischemic event a therapeutically effective amount of L-2-oxothiazolidine-4-carboxylic acid. In a further embodiment of the present invention, a method is provided for limiting ischemic reperfusion injury comprising the step of administering to a patient after the onset of an ischemic event a therapeutically effective amount of L-2-oxothiazolidine-4-carboxylic acid.

40 Claims, No Drawings

METHOD FOR TREATING REPERFUSION INJURY EMPLOYING L-2-OXOTHIAZOLIDINE-4-CARBOXYLIC ACID

BACKGROUND OF THE INVENTION

The present invention relates to a method and composition for treating reperfusion injury.

Ischemia refers to a condition wherein tissue suffers from a decrease or cessation of perfusion by blood. Ischemia can occur due to a blockage of the blood vessels, for example, due to atherosclerosis, heart attack, stroke, during organ transplant, or tissue necrosis as might be seen in liver disease.

Cardiac tissue is susceptible to ischemia and can be severely damaged by such an event. Accordingly, recovery from cardiac ischemia is critical in order to ensure proper cardiac function, which is related to survival of the patient. A cardiac ischemic event can be caused, for example, by heart attack or other disease states or from therapeutic intervention such as angioplasty or bypass surgery.

Although, a goal is to terminate an ischemic event, and to reestablish normal blood flow to the cells, the resultant reperfusion can result in a reperfusion injury damaging cells. A number of mechanisms have been proposed to explain reperfusion injury including: 1) cell swelling due to sodium and water influx; 2) calcium influx with resultant contraction bands and formation of calcium phosphate granules or crystals within mitochondria; 3) hemorrhage, secondary to vascular and/or microvascular injury; and 4) generation of a biologically significant quantity of oxygen free radicals. See, Flaherty, et al., *Reperfusion Injury*, Free Radical Biology & Medicine, Volume 5, pages 409–419, 1988.

Free radicals are molecules with an unpaired electron creating an unstable and highly reactive molecule. Oxygen free radicals are highly reactive with biological macromolecules such as are found in cell membranes, and thereby can induce cell damage.

Oxygen induced cell damage can occur in ischemic myocardium, as a result of reperfusion. A number of dysfunctions, which impair cardiac recovery after ischemia, have been shown to be associated with reperfusion, including: reperfusion arrhythmias; stunned myocardium; the "oxygen paradox"; and the development of infarction. See, Darley-Usmar, et al., *Oxygen and Reperfusion Damage: An Overview*, Free Rad. Res. Comms., Volume 7, No. 3–6 (1989).

There is increasing evidence that oxygen free radicals play a major role in the pathogenesis of reperfusion injury. See, Darly-Usmar and Flaherty, supra. The production of lipid peroxides and other active oxygen radicals during reperfusion are believed to result in tissue necrosis or damage.

Another focus of clinically significant ischemic/reperfusion injury is the intestines. This can occur in two principal ways. The first is caused by a hypoxic insult to the patient, for example in newborn infants who undergo difficult deliveries, or who are inadequately warmed just after delivery. In such patients and conditions it is believed that brief or prolonged periods of hypoxia can lead to intestinal ischemia. This, and subsequent reperfusion, can lead to a condition known as necrotizing enterocolitis (NEC), wherein the intestine in effect necroses, or rots, and must be partly or totally removed by surgical means.

Similarly, ischemia can be experienced by the intestine as when a blood clot, formed elsewhere in the body, travels and lodges in a major artery of the intestine. This thereby limits blood flow to the intestine. Resolution, or passing, of the clots can yield a reperfusion period and tissue damage.

Another example of ischemic/reperfusion injury is subsequent to cerebral blood clot and infarct. Cessation of blood flow damages adjacent tissue. Reperfusion, following administration of thrombolytics, can expand the size of the necrotic brain tissue.

Additional ischemic injuries may also occur in patients who are being prepared for artificial blood substitutes, either fluorocarbons or chemically modified hemoglobin. These patients are ischemic then exposed to high levels of oxygen provided by the blood substitute.

In all of the above conditions, the ischemic event and subsequent reperfusion are associated with damage to the organ, which can range in severity from minimal to fatal.

SUMMARY OF THE INVENTION

The present invention provides a method for treating and/or reducing ischemic reperfusion injury. To this end, in embodiment, a method for treating and/or reducing reperfusion injury is provided comprising the step of administering to a patient in danger of reperfusion injury a therapeutically effective amount of an agent that stimulates intracellular glutathione synthesis.

In an embodiment, a method is provided for limiting an expected ischemic reperfusion injury comprising the step of administering prior to an expected ischemic event a therapeutically effective amount of an agent that stimulates intracellular glutathione synthesis.

In a further embodiment of the present invention, a method is provided for limiting ischemic reperfusion injury comprising the step of administering to a patient at or after the onset of an ischemic event a therapeutically effective amount of an agent that stimulates intracellular glutathione synthesis.

In an embodiment, the agent is L-2-oxothiazolidine-4-carboxylate.

In an embodiment, the agent is a glutathione ester.

In an embodiment, the agent includes short-chain ethyl esters isopropyl esters of glutathione.

In an embodiment, the agent includes L-2-oxothiazolidine-4-carboxylate and glutathione esters.

In an embodiment, the agent is administered enternally.

In an embodiment, the agent is administered parenterally.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides a method for treating and/or limiting reperfusion injury. The method can be utilized as an adjunct to traditional cardiac therapy and for improving cardiac function after an ischemic event.

Generally, the method includes the step of administering a therapeutically effective amount of an agent that stimulates intracellular glutathione synthesis. The method of the present invention can be used either during or after an ischemic event, i.e., heart attack or stroke, to limit the reperfusion injury. Furthermore, the method of the present invention can be used prior to an expected ischemic event. To this end, the agent can be administered prior to a therapeutic intervention, e.g., cardiac bypass surgery or angioplasty.

By administering the agent prior to an expected ischemic event, intracellular glutathione synthesis can be stimulated so that the cells are preloaded with glutathione. The glutathione functions to limit the oxidative damage that results in tissue necrosis during reperfusion injury. The intracellular glutathione acts to reduce lipid peroxides, hydroperoxides, and other active oxygen species. Additionally, it is believed that glutathione can prevent or limit tissue damage if synthesis is stimulated at the start of reperfusion.

Because certain disease states and stress lower intracellular glutathione, stimulation of intracellular glutathione may be critical to not only elevating normal levels of intracellular glutathione, but to establish first a normal level of glutathione.

By administering the agent of the present invention oxidative damage from reperfusion is limited or prevented. The agent in the present invention can be any agent that stimulates intracellular glutathione synthesis. Examples of such agents are as follows: L-2-oxothiazolidine-4-carboxylate and glutathione esters. Likewise, other thiazolidine-4-carboxylate analogs can be utilized.

L-2-oxothiazolidine-4-carboxylate, in vivo, is subjected to the action of 5-oxo-L-prolinase in the presence of adenosine triphosphate to produce S-carboxyl cysteine. S-carboxyl cysteine is then decarboxylated to produce cysteine. Cysteine is then metabolized to produce glutathione. See, U.S. Pat. Nos.: 4,335,210; 4,434,158; 4,438,124; 4,647,571; and 4,665,082, the disclosures of which are incorporated herein by reference.

As previously stated, the agent can be a glutathione ester. For example, the agent can have the structure:

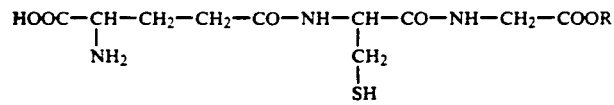

wherein R is an alkyl group containing 1 to 10 carbon atoms. Preferably the methyl ester or ethyl ester is used. Examples of these compounds are disclosed in U.S. Pat. No. 4,784,685, the disclosure of which is incorporated herein by reference.

As previously stated, the present invention can be used as an adjunct with other cardiac therapy. For example, the composition of the present invention can be given with a thrombolytic drug administered to a patient who has had a myocardial infarction.

Additionally, the composition can be given as an adjunct with compositions for the protection of the metabolic recovery of ischemic cardiac set forth in U.S. patent application Ser. No. 07/605,514, entitled "A METHOD AND COMPOSITION FOR PROTECTION OF A METABOLIC RECOVERY OF ISCHEMIC CARDIAC TISSUE", filed on Oct. 30, 1990, Ser. No. 605,514, and assigned to Assignee of this patent application.

An additional advantage of the present invention is that L-2-oxothiazolidine-4-carboxylate can penetrate the brain barrier. Therefore, the use of L-2-oxothiazolidine-4-carboxylate provides a method that can be used to prevent or reduce reperfusion injury to brain cells, for example, as a result of a stroke.

In an embodiment, the composition is administered at a dose of 5.0 to 500 mg/kg/day.

By way of example, and not limitation, experimental designs incorporating the present invention will now be given:

Experimental Design (Cardiac Ischemia)

Rat hearts were perfused in a non-recirculating retrograde (i.e., Langendorff) manner for 10 minutes before switching to an anterograde working heart mode for 25 minutes at which time baseline hemodynamics were recorded. The hearts were then subjected to 21.0 minutes of global no-flow ischemia (NFI). This was followed by 40 minutes of reperfusion in the working heart mode. Hearts were re-perfused with all solutions at 12-13 ml per minute.

Previous studies have demonstrated that peak recovery of hemodynamic function occurs at approximately 40 minutes reperfusion at this severity of ischemic challenge. The preload was set at 15 cm $H_2O$, the afterload at 80 cm $H_2O$ and the hearts were paced at 315 beats per minutes by a 2.2 Volt, 1.6 msec duration atrial stimulus.

Some hearts were perfused throughout the entire period, i.e., did not experience any ischemia. Some hearts were subjected to non-flow ischemia (NFI) as described above.

All hearts were perfused with 11 mM glucose in Krebs-Henseleit buffer (KHB), pH 7.4. Additionally, the hearts were perfused, in the following groups, with the following solutions:

| | |
|---|---|
| Group 1 | No ischemia; aerobic control. |
| Group 2 | No ischemia; Procysteine ™ (3% (w:v) L-2-oxothiazolidine-4-carboxylate in phosphate buffer) at a concentration of 500 micromoles/liter (500 μM). |
| Group 3 | No ischemia; Travasol ® (10% Amino Acid Injection) present at a concentration of 250 mg/l. |

The following groups were all subjected to no-flow ischemia (NFI).

| | | |
|---|---|---|
| Group 4 | NFI; | perfused throughout only with KHB; ischemic control. |
| Group 5 | NFI; | Procysteine ™ present throughout at 10 μM. |
| Group 6 | NFI; | Procysteine ™ present throughout at 25 μM. |
| Group 7 | NFI; | Procysteine ™ present throughout at 50 μM. |
| Group 8 | NFI; | Procysteine ™ present throughout at 250 μM. |
| Group 9 | NFI; | Procysteine ™ present throughout at 500 μM. |
| Group 10 | NFI; | Procysteine ™ present throughout at 1,000 μM. |
| Group 11 | NFI; | Travasol ® present throughout at 250 mg/L. |
| Group 12 | NFI; | as group 11, with Procysteine ™ throughout at 50 μM. |
| Group 13 | NFI; | as group 11, with Procysteine ™ throughout at 250 μM. |
| Group 14 | NFI; | as group 11, with Procysteine ™ throughout at 500 μM. |

The following Hemodynamic Parameters Were Measured:

1. Coronary flow [CF] ml/min [Cardiac perfusion]
2. Aortic flow [AO] ml/min [Systemic outflow]

3. Cardiac output [CO] ml/min [Total output]
4. Left Ventricular minute work [LVMW] g*m/min [cardiac work]
5. Left Ventricular Systolic Pressure [LVSP] mmHg [peak developed pressure; contractile apparatus performance]
6. Left Ventricular Diastolic Pressure [LVDP] mmHg [main resistive element to subendocardial perfusion]
7. Aortic Systolic Pressure [ASP] mmHg
8. Aortic Diastolic Pressure [ADP] mmHg (major determinant of coronary driving pressure)
9. Mean Aortic Pressure [MAP] mmHg [afterload]
10. Coronary Vascular Resistance [CVR] mmHg*min/ml [indicator of coronary patency e.g. elevated by osmotic swelling compression of the microvasculature by lysed cellular debris emboli]
11. Rate Pressure Product [RPP] mmHg/min [myocardial oxygen consumption Index]
12. Cardiac Efficiency Index [EFFI] g*m/mmHg [defined as work/$O_2$ consumed (i.e., EFF1=LVMW/RPP) indicates cardiac pump efficiency and oxygen wastage)
13. Recovery Time [RecT] min [duration of reperfusion required before an aortic outflow at 80 cm $H_2O$ is produced]
14. Initial Ischemic Mean Left Ventricular Pressure [LVP i] mmHg
15. Peak Ischemic Mean Left Ventricular Pressure [LVPmax i] mmHg
16. Final Ischemic Mean Left Ventricular Pressure [LVPf i] mmHg
17. Peak Amplitude Ischemic Contracture [ALVPpki] [contracture severity]
18. Post Peak Contracture Relaxation [ALVP post i] [contracture waning due to passive stretch from cytoskeletal distortion/disintegration]
19. Last beat, min [latency to arrest, oxygen reserve]
20. Latency to contracture onset [St*Cont] min [contracture onset delay]
21. Latency to contracture peak [Pk Cont] min [contracture onset delay]

The aerobic control group demonstrated a gradual increase in aortic flow, cardiac output, left ventricular min work, and cardiac efficiency index throughout the 70 min period while other hemodynamic parameters remained unaltered. This demonstrated that the preparation was stable throughout the time range considered in this study.

Pre-ischemic hemodynamics recorded in this investigation were similar to those recorded for healthy in vivo subjects, demonstrating the accuracy of the study.

Experimental conditions and pre-ischemic hemodynamics are presented for each experimental group in Table 1 (see below). No apparent differences exist between groups.

I. Pre-ischemic hemodynamics at 30 minutes

There was no significant alteration of baseline (pre-ischemic) hemodynamics due to either Travasol®, Procysteine TM, or a combination of both of these agents (Table 1).

II. Non-ischemic hemodynamics in hearts not subjected to NFI

Both Travasol® and Procysteine TM slightly enhance the augmentation of cardiac output, work, and efficiency developed at 40-70 minutes of perfusion (Table 2).

III. Ischemic contracture

No regimen specifically altered ischemic contracture time course (Table 3). Only Procysteine TM elicited a trend (somewhat dose-dependent) towards reduction of ischemic contracture amplitude. This was seen for Procysteine TM groups 500 µM and 1,000 µM.

IV. Post-ischemic recovery of hemodynamic function with Procysteine TM (Table 4)

All concentrations of Procysteine TM resulted in enhanced recovery of hemodynamic functions, including: cardiac perfusion (CF), outputs (AO, CO), work (LVMW), contractility (LVdP/dT), developed pressures (LVSP, ASP, MAP), oxygen consumption (kRPP), and cardiac efficiency (EFFI), while also reducing recovery time (Rec T). This broad spectrum of recovery indicates global myocardial salvaging. The enhanced functional recovery was significant at all time periods. The response was dose-related, with the optimal doses being 250 µM and 500 µM (Table 4).

V. Post-ischemic recover of hemodynamic function with Travasol® and combinations of Travasol® and Procysteine TM A. Travasol®

Treatment of hearts with Travasol® results in significant enhancement of post-ischemic recovery of hemodynamic functions (CF, AO, CO, LVMW, LVdPdT, LVSP, ASP, MAP, kRPP, EFFI, and Rec T). Most of the enhanced recovery of function was significant only at 20-40 minutes reperfusion.

B. Procysteine TM -Travasol® combinations (Table 5)

Co-treatment of hearts with Procysteine TM (50 µM, 250 µM, or 500 µM) plus Travasol® results in significant enhancement of the post-ischemic recovery of hemodynamic functions (CF, AO, CO, LVMW, LVdPdT, LVSP, ASP, MAP, CVR, kRPP, and EFFI) while reducing recovery time. The recovery was greater than that seen with Travasol® or Procysteine TM alone, and was generally evident at all time periods of reperfusion. These combination did not exhibit a dose-response. Therefore, the cardioprotective mechanism of Travasol® is at least partly distinct from that of Procysteine TM. In addition, recovery of function was greater at 10 minutes with Procysteine TM than with Travasol®.

TABLE 1

The effects of Procysteine TM and Travasol ® on pre-ischemic hemodynamics.

| GROUP | [PROCYSTEINE] | n | Body wt g | HR-P | CF | AO | CO | LVMW | LVSP | LVDP |
|---|---|---|---|---|---|---|---|---|---|---|
| 4 | 0 µM | 20 | 335 ± 4 | 315 ± 0 | 20.6 ± 0.4 | 67 ± 1 | 87 ± 1 | 71 ± 1 | 116 ± 1 | 12.8 ± 0.5 |
| 5 | 10 µM | 7 | 339 ± 5 | 315 ± 0 | 19.4 ± 0.6 | 72 ± 2 | 91 ± 2 | 74 ± 2 | 116 ± 2 | 13.3 ± 0.8 |
| 6 | 25 µM | 4 | 331 ± 10 | 315 ± 0 | 20.2 ± 1.0 | 66 ± 3 | 86 ± 3 | 68 ± 2 | 114 ± 3 | 13.1 ± 1.6 |
| 7 | 50 µM | 14 | 325 ± 5 | 315 ± 0 | 20.4 ± 0.7 | 69 ± 2 | 91 ± 2 | 73 ± 2 | 115 ± 2 | 12.9 ± 0.4 |
| 8 | 250 µM | 8 | 341 ± 3 | 315 ± 0 | 21.3 ± 0.5 | 70 ± 3 | 91 ± 3 | 75 ± 2 | 117 ± 1 | 13.8 ± 0.6 |
| 9 | 500 µM | 18 | 339 ± 4 | 315 ± 0 | 19.6 ± 0.5 | 68 ± 1 | 88 ± 1 | 71 ± 1 | 114 ± 1 | 13.2 ± 0.5 |
| 10 | 1 mM | 4 | 344 ± 3 | 315 ± 0 | 19.5 ± 1.2 | 65 ± 5 | 85 ± 6 | 67 ± 4 | 114 ± 3 | 11.9 ± 1.3 |
| 11 | Travasol | 4 | 331 ± 5 | 315 ± 0 | 19.3 ± 0.9 | 69 ± 2 | 88 ± 2 | 71 ± 2 | 117 ± 6 | 13.0 ± 0.2 |
| 12 | T + 50 µM | 4 | 340 ± 4 | 326 ± 13 | 19.9 ± 0.6 | 69 ± 5 | 89 ± 5 | 72 ± 4 | 115 ± 1 | 13.4 ± 0.5 |

TABLE 1-continued

| | | | | | | | | | | | |
|---|---|---|---|---|---|---|---|---|---|---|---|
| 13 | T + 250 μM | 6 | 336 ± 4 | 315 ± 0 | 20.9 ± 0.4 | 68 ± 1 | 89 ± 2 | | 73 ± 1 | 113 ± 1 | 12.8 ± 0.6 |
| 14 | T + 500 μM | 4 | 342 ± 6 | 315 ± 0 | 19.8 ± 1.3 | 65 ± 2 | 84 ± 3 | | 68 ± 2 | 111 ± 2 | 13.5 ± 1.2 |

| GROUP | [PROCYSTEINE] | n | LVdP/dT | ASP | ADP | MAP | CVR | kRPP | EFFI |
|---|---|---|---|---|---|---|---|---|---|
| 4 | 0 μM | 20 | 2735 ± 39 | 120 ± 1 | 29 ± 1 | 60 ± 0 | 2.3 ± 0.1 | 36.5 ± 0.4 | 1.9 ± 0.0 |
| 5 | 10 μM | 7 | 2777 ± 45 | 122 ± 2 | 28 ± 1 | 59 ± 1 | 2.4 ± 0.1 | 36.6 ± 0.6 | 2.0 ± 0.1 |
| 6 | 25 μM | 4 | 2865 ± 72 | 117 ± 2 | 29 ± 2 | 58 ± 1 | 2.2 ± 0.1 | 35.8 ± 1.0 | 1.9 ± 0.0 |
| 7 | 50 μM | 14 | 2618 ± 46 | 121 ± 1 | 30 ± 1 | 60 ± 0 | 2.4 ± 0.1 | 36.1 ± 0.5 | 2.0 ± 0.0 |
| 8 | 250 μM | 8 | 2723 ± 47 | 122 ± 2 | 30 ± 1 | 61 ± 0 | 2.2 ± 0.1 | 36.7 ± 0.3 | 2.0 ± 0.0 |
| 9 | 500 μM | 18 | 2538 ± 48 | 120 ± 1 | 29 ± 0 | 60 ± 0 | 2.3 ± 0.1 | 36.0 ± 0.4 | 2.0 ± 0.0 |
| 10 | 1 mM | 4 | 2761 ± 78 | 118 ± 2 | 28 ± 3 | 58 ± 2 | 2.4 ± 0.2 | 35.8 ± 0.9 | 1.9 ± 0.1 |
| 11 | Travasol | 4 | 2687 ± 109 | 122 ± 2 | 28 ± 0 | 59 ± 1 | 2.4 ± 0.1 | 36.8 ± 1.9 | 1.9 ± 0.1 |
| 12 | T + 50 μM | 4 | 2558 ± 62 | 120 ± 1 | 30 ± 1 | 60 ± 1 | 2.3 ± 0.1 | 37.5 ± 1.5 | 1.9 ± 0.0 |
| 13 | T + 250 μM | 6 | 2576 ± 53 | 121 ± 1 | 30 ± 1 | 60 ± 1 | 2.3 ± 0.1 | 35.5 ± 0.4 | 2.1 ± 0.0 |
| 14 | T + 500 μM | 4 | 2642 ± 91 | 120 ± 3 | 29 ± 1 | 59 ± 1 | 2.3 ± 0.1 | 35.0 ± 0.6 | 1.9 ± 0.1 |

TABLE 2

The effects of Procysteine ™ and Travasol ® on percent recovery of hemodynamic functions during 70 minutes non-ischemic heart perfusion. Percent recoveries are relative to baseline hemodynamics at 30 minutes perfusion.

| Group | 1 | 2 | 3 |
|---|---|---|---|
| Treatment | None | Procysteine ™ 500 μM | Travasol ® 2.5 ml/l |
| n | 10 | 10 | 10 |
| % CF-40 | 103 ± 1 | 100 ± 1 | 103 ± 1 |
| % CF-50 | 102 ± 2 | 104 ± 3 | 105 ± 2 |
| % CF-60 | 102 ± 2 | 106 ± 4 | 104 ± 1 |
| % CF-70 | 101 ± 1 | 106 ± 5 | 104 ± 2 |
| % AO-40 | 100 ± 1 | 100 ± 1 | 102 ± 1 |
| % AO-50 | 99 ± 2 | 102 ± 1 | 103 ± 1 |
| % AO-60 | 100 ± 1 | 103 ± 1 | 105 ± 1 |
| % AO-70 | 101 ± 2 | 105 ± 1 | 106 ± 1 |
| % CO-40 | 100 ± 1 | 100 ± 1 | 102 ± 1 |
| % CO-50 | 100 ± 2 | 102 ± 1 | 104 ± 1 |
| % CO-60 | 100 ± 2 | 104 ± 1 | 104 ± 1 |
| % CO-70 | 101 ± 2 | 105 ± 1 | 106 ± 1 |
| % LVMW-40 | 101 ± 1 | 100 ± 1 | 102 ± 1 |
| % LVMW-50 | 101 ± 1 | 103 ± 1 | 104 ± 1 |
| % LVMW-60 | 102 ± 2 | 105 ± 1 | 105 ± 1 |
| % LVMW-70 | 102 ± 1 | 106 ± 1 | 107 ± 1 |
| % LVSP-40 | 101 ± 1 | 100 ± 0 | 101 ± 0 |
| % LVSP-50 | 101 ± 1 | 101 ± 1 | 101 ± 0 |
| % LVSP-60 | 102 ± 1 | 101 ± 1 | 102 ± 1 |
| % LVSP-70 | 102 ± 1 | 101 ± 1 | 102 ± 1 |
| % LVDP-40 | 100 ± 1 | 95 ± 5 | 103 ± 1 |
| % LVDP-50 | 102 ± 2 | 97 ± 6 | 106 ± 2 |
| % LVDP-60 | 102 ± 3 | 98 ± 5 | 106 ± 2 |
| % LVDP-70 | 106 ± 3 | 98 ± 5 | 105 ± 3 |
| % LVdP/dT-40 | 100 ± 1 | 100 ± 1 | 101 ± 0 |
| % LVdP/dT-50 | 100 ± 0 | 102 ± 1 | 102 ± 1 |
| % LVdP/dT-60 | 102 ± 1 | 102 ± 1 | 102 ± 1 |
| % LVdP/dT-70 | 101 ± 0 | 102 ± 1 | 102 ± 1 |
| % ASP-40 | 99 ± 0 | 99 ± 0 | 100 ± 0 |
| % ASP-50 | 98 ± 0 | 99 ± 0 | 99 ± 0 |
| % ASP-60 | 98 ± 0 | 98 ± 1 | 98 ± 1 |
| % ASP-70 | 98 ± 0 | 98 ± 0 | 98 ± 0 |
| % MAP-40 | 101 ± 0 | 100 ± 0 | 100 ± 0 |
| % MAP-50 | 102 ± 0 | 101 ± 1 | 101 ± 0 |
| % MAP-60 | 102 ± 0 | 101 ± 0 | 100 ± 0 |
| % MAP-70 | 102 ± 0 | 101 ± 0 | 101 ± 1 |
| % CVR-40 | 97 ± 1 | 104 ± 4 | 97 ± 1 |
| % CVR-50 | 100 ± 3 | 99 ± 5 | 96 ± 2 |
| % CVR-60 | 101 ± 3 | 98 ± 5 | 95 ± 2 |
| % CVR-70 | 100 ± 2 | 100 ± 6 | 97 ± 2 |
| % kRPP-40 | 101 ± 1 | 100 ± 0 | 101 ± 0 |
| % kRPP-50 | 101 ± 1 | 101 ± 1 | 101 ± 0 |
| % kRPP-60 | 102 ± 1 | 101 ± 1 | 101 ± 1 |
| % kRPP-70 | 102 ± 1 | 101 ± 1 | 102 ± 1 |
| % EFFI-40 | 100 ± 1 | 100 ± 1 | 102 ± 1 |
| % EFFI-50 | 100 ± 1 | 102 ± 1 | 103 ± 1 |
| % EFFI-60 | 100 ± 1 | 104 ± 1 | 103 ± 1 |
| % EFFI-70 | 101 ± 1 | 105 ± 1 | 105 ± 1 |

TABLE 3

The effects of Procysteine ™ and Travasol ® (T) on ischemic contracture.

| Group | [Procysteine ™] | n | LVP | LVPmax | LVP | StCont | PkCont | last beat | ΔLVP pk | ΔLVP po |
|---|---|---|---|---|---|---|---|---|---|---|
| 4 | 0 μM | 10 | 11 ± 0 | 33 ± 4 | 27 ± 4 | 15 ± 1 | 18 ± 0 | 120 ± 11 | 24 ± 4 | −6 ± 1 |
| 5 | 10 μM | 7 | 10 ± 1 | 32 ± 3 | 23 ± 2 | 14 ± 1 | 18 ± 1 | 115 ± 9 | 22 ± 3 | −8 ± 3 |
| 6 | 25 μM | 4 | 10 ± 1 | 40 | 28 | 14 ± 1 | 16 | 120 ± 18 | 30 | −12 |
| 7 | 50 μM | 14 | 10 ± 0 | 31 ± 4 | 25 ± 3 | 14 ± 1 | 18 ± 1 | 118 ± 9 | 22 ± 3 | −7 ± 2 |
| 8 | 250 μM | 8 | 11 ± 0 | 33 ± 2 | 26 ± 2 | 15 ± 1 | 18 ± 1 | 109 ± 8 | 23 ± 2 | −7 ± 1 |
| 9 | 500 μM | 8 | 11 ± 0 | 23 ± 2 | 18 ± 2 | 14 ± 1 | 17 ± 1 | 125 ± 6 | 12 ± 2 | −5 ± 2 |
| 10 | 1 mM | 4 | 10 ± 1 | 18 ± 1 | 14 ± 2 | 16 ± 1 | 17 ± 1 | 106 ± 9 | 9 ± 1 | −8 ± 5 |
| 11 | Travasol ® | 4 | 11 ± 0 | 38 ± 7 | 27 ± 6 | 14 ± 1 | 17 ± 1 | 108 ± 14 | 27 ± 8 | −11 ± 3 |
| 12 | T + 50 μm Procysteine ™ | 4 | 10 ± 1 | 33 ± 7 | 27 ± 7 | 15 ± 1 | 19 ± 1 | 108 ± 5 | 23 ± 7 | −6 ± 3 |
| 13 | T + 250 μm Procysteine ™ | 6 | 10 ± 0 | 26 ± 5 | 23 ± 4 | 16 ± 0 | 19 ± 0 | 118 ± 12 | 16 ± 5 | −3 ± 1 |
| 14 | T + 500 μm Procysteine ™ | 4 | 10 ± 0 | 28 ± 5 | 22 ± 5 | 15 ± 1 | 18 ± 1 | 116 ± 9 | 17 ± 5 | −6 ± 3 |

TABLE 4

Percent recovery of hemodynamic functions and recovery times during 40 minutes post-ischemia reperfusion. Dose response in Procysteine ™-treated groups.

| Group | 4 | 5 | 6 | 7 | 8 | 9 | 10 |
|---|---|---|---|---|---|---|---|
| [Procysteine ™] | 0 μM | 10 μM | 25 μM | 50 μM | 250 μM | 500 μM | 1 mM |
| n | 10 | 7 | 4 | 14 | 8 | 8 | 4 |
| % CF-10 | 17 ± 4 | 41 ± 11 | 20 ± 3 | 41 ± 9 | 48 ± 12 | 55 ± 12 | 47 ± 23 |
| % CF-20 | 17 ± 5 | 36 ± 9 | 34 ± 13 | 42 ± 7 | 56 ± 11 | 51 ± 12 | 52 ± 14 |
| % CF-30 | 23 ± 5 | 44 ± 10 | 38 ± 10 | 51 ± 7 | 58 ± 9 | 54 ± 12 | 53 ± 16 |
| % CF-40 | 28 ± 6 | 53 ± 11 | 45 ± 6 | 58 ± 6 | 66 ± 8 | 63 ± 10 | 62 ± 13 |
| % AO-10 | 0 ± 0 | 7 ± 4 | 0 ± 0 | 11 ± 5 | 11 ± 5 | 19 ± 9 | 8 ± 7 |
| % AO-20 | 0 ± 0 | 4 ± 2 | 7 ± 8 | 16 ± 5 | 18 ± 8 | 23 ± 12 | 12 ± 11 |
| % AO-30 | 2 ± 1 | 10 ± 5 | 13 ± 10 | 20 ± 6 | 24 ± 9 | 28 ± 12 | 22 ± 12 |
| % AO-40 | 6 ± 4 | 15 ± 6 | 20 ± 9 | 28 ± 6 | 33 ± 9 | 35 ± 11 | 27 ± 12 |
| % CO-10 | 4 ± 1 | 14 ± 5 | 5 ± 1 | 18 ± 6 | 19 ± 6 | 27 ± 9 | 17 ± 10 |
| % CO-20 | 4 ± 1 | 11 ± 3 | 14 ± 9 | 22 ± 6 | 27 ± 8 | 30 ± 11 | 21 ± 11 |
| % CO-30 | 7 ± 2 | 17 ± 5 | 19 ± 10 | 27 ± 6 | 32 ± 8 | 34 ± 11 | 29 ± 12 |
| % CO-40 | 11 ± 4 | 23 ± 6 | 26 ± 8 | 35 ± 6 | 41 ± 9 | 41 ± 10 | 35 ± 12 |
| % LVMW-10 | 3 ± 1 | 14 ± 6 | 3 ± 1 | 18 ± 7 | 20 ± 7 | 29 ± 10 | 19 ± 12 |
| % LVMW-20 | 3 ± 1 | 11 ± 4 | 14 ± 11 | 24 ± 6 | 29 ± 9 | 31 ± 12 | 24 ± 12 |
| % LVMW-30 | 6 ± 2 | 19 ± 6 | 20 ± 12 | 30 ± 7 | 31 ± 7 | 36 ± 12 | 32 ± 14 |
| % LVMW-40 | 11 ± 4 | 25 ± 7 | 30 ± 9 | 38 ± 6 | 44 ± 9 | 45 ± 11 | 40 ± 13 |
| % LVSP-10 | 36 ± 5 | 51 ± 11 | 38 ± 12 | 54 ± 9 | 61 ± 11 | 66 ± 11 | 60 ± 17 |
| % LVSP-20 | 38 ± 4 | 55 ± 8 | 52 ± 13 | 64 ± 7 | 72 ± 6 | 69 ± 10 | 66 ± 11 |
| % LVSP-30 | 45 ± 7 | 63 ± 8 | 56 ± 15 | 73 ± 6 | 77 ± 5 | 76 ± 7 | 70 ± 12 |
| % LVSP-40 | 49 ± 8 | 72 ± 6 | 72 ± 5 | 81 ± 4 | 84 ± 3 | 83 ± 6 | 78 ± 8 |
| % LVDP-10 | 170 ± 34 | 130 ± 7 | 138 ± 17 | 135 ± 6 | 131 ± 6 | 107 ± 6 | 151 ± 20 |
| % LVDP-20 | 157 ± 22 | 136 ± 5 | 136 ± 19 | 142 ± 6 | 124 ± 6 | 118 ± 6 | 151 ± 27 |
| % LVDP-30 | 162 ± 22 | 128 ± 4 | 134 ± 16 | 139 ± 9 | 129 ± 5 | 122 ± 5 | 148 ± 19 |
| % LVDP-40 | 159 ± 22 | 128 ± 2 | 122 ± 23 | 136 ± 9 | 117 ± 7 | 119 ± 3 | 139 ± 14 |
| % LVdP/dT-10 | 22 ± 5 | 40 ± 13 | 26 ± 14 | 47 ± 10 | 55 ± 13 | 49 ± 14 | 52 ± 21 |
| % LVdP/dT-20 | 26 ± 4 | 46 ± 11 | 36 ± 14 | 58 ± 7 | 67 ± 8 | 64 ± 12 | 56 ± 12 |
| % LVdP/dT-30 | 34 ± 7 | 58 ± 12 | 43 ± 15 | 68 ± 7 | 74 ± 7 | 74 ± 8 | 60 ± 13 |
| % LVdP/dT-40 | 40 ± 8 | 70 ± 8 | 65 ± 5 | 76 ± 5 | 84 ± 4 | 80 ± 7 | 71 ± 9 |
| % ASP-10 | 36 ± 2 | 53 ± 9 | 32 ± 4 | 51 ± 7 | 58 ± 8 | 65 ± 9 | 58 ± 13 |
| % ASP-20 | 36 ± 3 | 58 ± 6 | 53 ± 14 | 61 ± 6 | 68 ± 6 | 66 ± 8 | 64 ± 10 |
| % ASP-30 | 46 ± 5 | 64 ± 5 | 60 ± 13 | 69 ± 4 | 73 ± 4 | 72 ± 7 | 69 ± 11 |
| % ASP-40 | 50 ± 6 | 68 ± 4 | 74 ± 6 | 76 ± 3 | 79 ± 3 | 77 ± 6 | 75 ± 8 |
| % MAP-10 | 67 ± 4 | 89 ± 11 | 60 ± 8 | 80 ± 8 | 90 ± 11 | 96 ± 11 | 91 ± 17 |
| % MAP-20 | 66 ± 6 | 100 ± 9 | 86 ± 18 | 94 ± 6 | 104 ± 6 | 99 ± 7 | 102 ± 11 |
| % MAP-30 | 82 ± 8 | 106 ± 6 | 94 ± 17 | 104 ± 4 | 102 ± 7 | 105 ± 6 | 104 ± 12 |
| % MAP-40 | 85 ± 8 | 106 ± 3 | 114 ± 2 | 109 ± 2 | 112 ± 2 | 106 ± 4 | 109 ± 4 |
| % CVR*-10 | 310 ± 67 | 335 ± 166 | 173 ± 40 | 233 ± 39 | 202 ± 43 | 217 ± 37 | 209 ± 51 |
| % CVR*-20 | 333 ± 79 | 488 ± 237 | 233 ± 39 | 253 ± 32 | 227 ± 44 | 251 ± 55 | 184 ± 26 |
| % CVR*-30 | 313 ± 42 | 399 ± 175 | 238 ± 89 | 213 ± 20 | 198 ± 37 | 242 ± 45 | 203 ± 47 |
| % CVR*-40 | 286 ± 36 | 239 ± 56 | 260 ± 33 | 196 ± 19 | 188 ± 30 | 186 ± 28 | 176 ± 39 |
| % kRPP-10 | 36 ± 5 | 51 ± 11 | 38 ± 11 | 54 ± 9 | 61 ± 11 | 66 ± 11 | 60 ± 71 |
| % kRPP-20 | 38 ± 4 | 55 ± 8 | 52 ± 13 | 64 ± 7 | 72 ± 6 | 69 ± 10 | 66 ± 11 |
| % kRPP-30 | 45 ± 7 | 63 ± 8 | 56 ± 15 | 73 ± 6 | 77 ± 5 | 76 ± 7 | 70 ± 12 |
| % kRPP-40 | 49 ± 8 | 72 ± 6 | 72 ± 5 | 81 ± 4 | 84 ± 3 | 83 ± 6 | 78 ± 8 |
| % EFFI-10 | 8 ± 1 | 21 ± 7 | 8 ± 2 | 23 ± 7 | 26 ± 8 | 36 ± 10 | 24 ± 13 |
| % EFFI-20 | 7 ± 2 | 18 ± 5 | 21 ± 13 | 29 ± 7 | 35 ± 9 | 36 ± 12 | 31 ± 13 |
| % EFFI-30 | 12 ± 2 | 26 ± 7 | 30 ± 14 | 35 ± 7 | 37 ± 8 | 41 ± 12 | 41 ± 15 |
| % EFFI-40 | 17 ± 5 | 32 ± 8 | 40 ± 11 | 44 ± 6 | 51 ± 9 | 49 ± 10 | 48 ± 14 |
| % VFib | 34 ± 4 | 49 ± 12 | 72 ± 14 | 43 ± 7 | 44 ± 7 | 38 ± 8 | 26 ± 6 |
| Rec-t | 33 ± 2 | 17 ± 5 | 28 ± 8 | 18 ± 4 | 16 ± 5 | 13 ± 5 | 15 ± 8 |
| % Rec | 30 | 71 | 75 | 79 | 100 | 88 | 75 |

TABLE 5

Percent recovery of hemodynamic functions and recovery times during 40 minutes post-ischemic reperfusion. Comparative efficiency of Travasol ®, Procysteine ™, and Travasol ® + Procysteine ™ treatments.

| [Procysteine] | 0 μM | 0 μM | 50 μM | 250 μM | 500 μM | 50 μM | 250 μM | 500 μM |
|---|---|---|---|---|---|---|---|---|
| [Travasol ®] | 0 | 2.5 ml/L | 0 | 0 | 0 | 2.5 ml/L | 2.5 ml/L | 2.5 ml/L |
| n | 10 | 4 | 14 | 8 | 8 | 4 | 6 | 4 |
| % CF-10 | 17 ± 4 | 18 ± 6 | 41 ± 9 | 48 ± 12 | 55 ± 12 | 28 ± 5 | 44 ± 16 | 34 ± 21 |
| % CF-20 | 17 ± 5 | 60 ± 13 | 42 ± 7 | 56 ± 11 | 51 ± 12 | 82 ± 3 | 82 ± 8 | 71 ± 9 |
| % CF-30 | 23 ± 5 | 63 ± 9 | 51 ± 7 | 58 ± 9 | 54 ± 12 | 81 ± 4 | 83 ± 7 | 71 ± 10 |
| % CF-40 | 28 ± 6 | 62 ± 10 | 58 ± 6 | 66 ± 8 | 63 ± 10 | 80 ± 5 | 83 ± 8 | 73 ± 7 |
| % AO-10 | 0 ± 0 | 0 ± 0 | 11 ± 5 | 11 ± 5 | 19 ± 9 | 0 ± 0 | 15 ± 13 | 13 ± 15 |
| % AO-20 | 0 ± 0 | 12 ± 5 | 16 ± 5 | 18 ± 8 | 23 ± 12 | 45 ± 3 | 36 ± 13 | 30 ± 14 |
| % AO-30 | 2 ± 1 | 23 ± 9 | 20 ± 6 | 24 ± 9 | 28 ± 12 | 59 ± 1 | 48 ± 13 | 52 ± 1 |
| % AO-40 | 6 ± 4 | 27 ± 11 | 28 ± 6 | 33 ± 9 | 35 ± 11 | 62 ± 1 | 54 ± 11 | 58 ± 1 |
| % CO-10 | 4 ± 1 | 4 ± 2 | 18 ± 6 | 19 ± 6 | 27 ± 9 | 6 ± 1 | 22 ± 13 | 18 ± 17 |
| % CO-20 | 4 ± 1 | 22 ± 7 | 22 ± 6 | 27 ± 8 | 30 ± 11 | 53 ± 3 | 47 ± 12 | 40 ± 13 |
| % CO-30 | 7 ± 2 | 32 ± 9 | 27 ± 6 | 32 ± 8 | 34 ± 11 | 64 ± 2 | 56 ± 11 | 56 ± 11 |
| % CO-40 | 11 ± 4 | 34 ± 11 | 35 ± 6 | 41 ± 9 | 41 ± 10 | 66 ± 2 | 60 ± 10 | 62 ± 10 |
| % LVMW-10 | 3 ± 1 | 3 ± 2 | 18 ± 7 | 20 ± 7 | 29 ± 10 | 5 ± 2 | 22 ± 14 | 18 ± 18 |
| % LVMW-20 | 3 ± 1 | 26 ± 8 | 24 ± 6 | 29 ± 9 | 31 ± 12 | 58 ± 3 | 50 ± 12 | 44 ± 13 |
| % LVMW-30 | 6 ± 2 | 36 ± 10 | 30 ± 7 | 31 ± 7 | 36 ± 12 | 69 ± 1 | 60 ± 11 | 62 ± 10 |
| % LVMW-40 | 11 ± 4 | 39 ± 12 | 38 ± 6 | 44 ± 9 | 45 ± 11 | 71 ± 1 | 64 ± 10 | 67 ± 9 |
| % LVSP-10 | 36 ± 5 | 32 ± 10 | 54 ± 9 | 61 ± 11 | 66 ± 11 | 48 ± 12 | 56 ± 16 | 48 ± 20 |
| % LVSP-20 | 38 ± 4 | 81 ± 5 | 64 ± 7 | 72 ± 6 | 69 ± 10 | 90 ± 2 | 90 ± 4 | 88 ± 5 |
| % LVSP-30 | 45 ± 7 | 86 ± 6 | 73 ± 6 | 77 ± 7 | 76 ± 7 | 95 ± 1 | 96 ± 4 | 95 ± 3 |
| % LVSP-40 | 49 ± 8 | 88 ± 5 | 81 ± 4 | 84 ± 3 | 83 ± 6 | 95 ± 1 | 97 ± 3 | 96 ± 4 |
| % LVDP-10 | 170 ± 34 | 145 ± 15 | 135 ± 6 | 131 ± 6 | 107 ± 6 | 123 ± 5 | 137 ± 12 | 132 ± 14 |
| % LVDP-20 | 157 ± 22 | 132 ± 13 | 142 ± 6 | 124 ± 6 | 118 ± 6 | 110 ± 13 | 110 ± 4 | 124 ± 13 |
| % LVDP-30 | 162 ± 22 | 129 ± 10 | 139 ± 9 | 129 ± 5 | 122 ± 5 | 107 ± 13 | 115 ± 4 | 125 ± 10 |
| % LVDP-40 | 159 ± 22 | 130 ± 10 | 136 ± 10 | 117 ± 7 | 119 ± 3 | 112 ± 1 | 112 ± 7 | 126 ± 13 |
| % LVdP/dT-10 | 22 ± 5 | 18 ± 12 | 47 ± 10 | 55 ± 13 | 49 ± 14 | 44 ± 16 | 44 ± 18 | 38 ± 25 |
| % LVdP/dT-20 | 26 ± 4 | 74 ± 16 | 58 ± 7 | 67 ± 8 | 64 ± 12 | 90 ± 3 | 88 ± 5 | 87 ± 7 |
| % LVdP/dT-30 | 34 ± 7 | 84 ± 11 | 68 ± 7 | 74 ± 7 | 74 ± 8 | 94 ± 3 | 95 ± 4 | 94 ± 5 |
| % LVdP/dT-40 | 40 ± 8 | 85 ± 10 | 76 ± 5 | 84 ± 4 | 80 ± 7 | 06 ± 2 | 96 ± 4 | 92 ± 6 |
| % ASP-10 | 36 ± 2 | 33 ± 6 | 51 ± 7 | 58 ± 8 | 65 ± 9 | 47 ± 10 | 52 ± 13 | 48 ± 16 |
| % ASP-20 | 36 ± 3 | 70 ± 7 | 61 ± 6 | 68 ± 6 | 66 ± 8 | 86 ± 3 | 81 ± 3 | 80 ± 3 |
| % ASP-30 | 46 ± 5 | 78 ± 4 | 69 ± 4 | 73 ± 4 | 72 ± 7 | 89 ± 2 | 86 ± 3 | 87 ± 2 |
| % ASP-40 | 50 ± 6 | 79 ± 5 | 76 ± 3 | 79 ± 3 | 77 ± 6 | 89 ± 11 | 86 ± 2 | 88 ± 2 |
| % MAP-10 | 67 ± 4 | 62 ± 10 | 80 ± 8 | 90 ± 11 | 96 ± 1 | 80 ± 15 | 77 ± 15 | 75 ± 15 |
| % MAP-20 | 66 ± 6 | 108 ± 6 | 94 ± 6 | 104 ± 6 | 99 ± 7 | 109 ± 1 | 109 ± 2 | 112 ± 3 |
| % MAP-30 | 82 ± 8 | 114 ± 1 | 104 ± 4 | 102 ± 7 | 105 ± 6 | 108 ± 11 | 109 ± 3 | 110 ± 3 |
| % MAP-40 | 85 ± 8 | 114 ± 1 | 109 ± 2 | 112 ± 2 | 106 ± 4 | 108 ± 2 | 108 ± 2 | 110 ± 2 |
| % CVR*-10 | 310 ± 67 | 202 ± 16 | 233 ± 39 | 202 ± 43 | 217 ± 37 | 231 ± 47 | 146 ± 29 | 234 ± 52 |
| % CVR*-20 | 333 ± 79 | 187 ± 37 | 253 ± 32 | 227 ± 44 | 251 ± 55 | 132 ± 9 | 140 ± 20 | 159 ± 25 |
| % CVR*-30 | 313 ± 42 | 185 ± 33 | 213 ± 20 | 198 ± 37 | 242 ± 45 | 133 ± 8 | 135 ± 18 | 160 ± 27 |
| % CVR*-40 | 286 ± 36 | 192 ± 38 | 196 ± 19 | 188 ± 30 | 186 ± 28 | 134 ± 1 | 135 ± 17 | 149 ± 18 |
| % kRPP-10 | 36 ± 5 | 32 ± 10 | 54 ± 9 | 61 ± 11 | 66 ± 1 | 46 ± 1 | 56 ± 16 | 48 ± 20 |
| % kRPP-20 | 38 ± 4 | 81 ± 5 | 65 ± 7 | 72 ± 6 | 69 ± 10 | 88 ± 3 | 90 ± 4 | 88 ± 5 |
| % kRPP-30 | 45 ± 7 | 86 ± 6 | 73 ± 6 | 77 ± 5 | 76 ± 7 | 92 ± 4 | 96 ± 4 | 96 ± 3 |
| % kRPP-40 | 49 ± 8 | 88 ± 5 | 81 ± 4 | 84 ± 3 | 83 ± 6 | 92 ± 4 | 96 ± 3 | 96 ± 4 |
| % EFFI-10 | 8 ± 1 | 7 ± 1 | 23 ± 7 | 26 ± 8 | 36 ± 10 | 12 ± 2 | 26 ± 13 | 22 ± 18 |
| % EFFI-20 | 7 ± 2 | 30 ± 9 | 29 ± 7 | 35 ± 9 | 36 ± 12 | 66 ± 5 | 54 ± 11 | 48 ± 12 |
| % EFFI-30 | 12 ± 2 | 40 ± 11 | 35 ± 7 | 37 ± 8 | 41 ± 12 | 76 ± 4 | 61 ± 9 | 64 ± 9 |
| % EFFI-40 | 17 ± 5 | 44 ± 12 | 44 ± 6 | 51 ± 9 | 49 ± 10 | 78 ± 4 | 66 ± 8 | 69 ± 7 |
| μVFib | 34 ± 4 | 55 ± 6 | 43 ± 7 | 44 ± 7 | 38 ± 8 | 53 ± 6 | 36 ± 11 | 52 ± 7 |
| Rec-T | 33 ± 2 | 20 ± 6 | 18 ± 4 | 16 ± 5 | 13 ± 5 | 13 ± 1 | 12 ± 2 | 15 ± 3 |
| % Rec | 30 | 100 | 79 | 100 | 88 | 100 | 100 | 100 |

Experimental Design (Intestinal Ischemia)

Experiments were performed to demonstrate the effects of stimulation of intracellular synthesis of glutathione on intestinal ischemia. Newborn piglets (~1kg) were anesthetized prior to surgery. First a catheter was placed in the jugular vein and secured therein. As soon as this was complete, Procysteine ™ (3% w:v L-2-oxo-thiazolidine-4-carboxylate, pH 7.0 in phosphate buffer) was infused at a rate of 16.5 ml/hour.

The second surgical step involved making a small incision in the lower abdomen; the mesenteric artery was occluded by clamping for 40–45 minutes. This procedure rendered the intestine almost completely ischemic, after which clamps were removed and blood flow was allowed to resume. The incision was closed.

The infusion of Procysteine ™ was terminated at the end of two hours. Control piglets received only an infusion of phosphate buffer.

The piglets were infused daily with Procysteine ™ or buffer, but they ate normal food orally. On the fifth day of the experiment all piglets were sacrificed. Samples were taken of tissue from several levels of the large and small intestines and, especially in areas where gross abnormality was observed. Histopathological examinations of the intestines were carried out by an experienced pathologist.

Results of the experiments are summarized as follows:
Incidence of intestinal histopathology:
Three of four control piglets (75%),
Three of thirteen piglets receiving Procysteine ™ (23%).

Severity of intestinal lesions was graded on a scale, with zero ("0") being no pathology, and eight ("8") being the most severe pathology.

Three Control piglets: values were 4, 6, and 8;

Three Procysteine TM piglets: values were 3, 3, and 4.

Obviously, Procysteine TM infusion reduced both the incidence and severity of intestinal lesions related to induced ischemia.

By way of example, and not limitation, contemplated examples in the present invention will now be set forth.

EXAMPLE ONE

This contemplated example demonstrates the use of the composition and method of the present invention as a therapy for a patient having ischemic cardiac tissue. The method limits the ischemic reperfusion injury.

A middle aged male patient is admitted to intensive care following acute myocardial infarction. A thrombolytic drug was immediately administered intravenously to the patient.

In conjunction with the drug infusion, a Procysteine TM solution, suitable for injection and having the following composition: 3% (w:v) solution L-2-oxothiazolidine-4-carboxylate in a sodium phosphate buffer, final pH being adjusted to 7.0, was infused at a rate of 25 ml/hour. The infusion was continued until 100 ml of solution was infused.

During the above period the patient was managed as follows. The heart was monitored by continuous EKG recording. Serial blood samples were taken at 1-1.5 hour intervals, for the measurement of creatine phosphokinase (CPK). The enzyme, CPK, is released from damaged heart cells, and is a rough index of the degree of injury severity and recovery.

It was observed that the EKG showed minimal evidence of reperfusion arrythmias, with a return to a reasonably normal pattern in 6-7 hours. Other patients with attacks of similar severity, but not treated with Procysteine TM, usually demonstrated substantial evidence of reperfusion arrythmias and a return to acceptable patterns only after 8 to 10 hours.

Blood levels of CPK would have been expected to peak at about 10 hours; in this patient it peaked at 6 to 7 hours.

The patient was discharged from the ICU in 2 days, and from the hospital 2 days thereafter. Subsequent testing showed recovery of the damaged myocardium to a greater degree than would have been seen in patients not infused with substrate.

EXAMPLE TWO

This contemplated example demonstrates the use of the composition and method of the present invention as a therapy prior to an ischemic event.

A middle-aged male underwent an angioplasty. Prior to insertion of a balloon catheter into the coronary artery, the patient was started on an I.V. infusion consisting of 3% (mix) (w:v) L-2-oxothiazolidine-4-carboxylate at a rate of 25 ml/hr. Infusion continued during the entire period of angioplasty. A balloon catheter was then placed so as to be surrounded by atheroma in an artery leading to the heart. The balloon was expanded to push the atheroma into the intima. The balloon was then partially deflated, moved downstream to the next section of atheroma, and the procedure repeated. The total time of near-total interruption of flow through this vessel, due to the angioplasty procedure per se, was one hour and 20 minutes.

Immediately upon removing the balloon portion of the catheter an infusion consisting of 3% (w:v) L-2-oxothiazolidine-4-carboxylate in a sodium phosphate buffer was begun, through the lumen of the catheter. In this manner, a portion of the heart was rather directly perfused with the composition for 20 minutes. The entire catheter was then removed so as to allow blood flow to return to the heart. The substrate infusion continued via a peripheral vein until the infusion of 100 ml of solution was completed.

Considering the degree of atheromatous occlusion and the duration of the angioplasty procedure, clinical experience led the cardiologist to predict that the patient would have significant abnormalities of the EKG for several hours following the procedure. However, infusion of the substrate seemed to allow the heart to evolve to a reasonably normal EKG in less time than expected. Hemodynamic parameters also reflected a return to normal in an accelerated time. The patient experienced no problems and was discharged that evening.

EXAMPLE THREE

A male infant was born several weeks prematurely, and the delivery was difficult. Feeding by the intravenous route was instituted on the second day of life. On the fourth day the infant was in distress, and showed signs of intestinal involvement. An x-ray showed that the intestine was distended with large pockets of gas. A presumed diagnosis was for the occurrence of necrotizing enterocolitis (NEC).

The physician immediately ordered the infant to begin receiving L-2-oxothiazolidine-4-carboxylate. The drug was admixed with the parenteral nutrition solution. It was present at a concentration of 150 mg/L; the dosage was 100 mg/kg body weight/day, and was continued for ten days. Frequent x-rays over this time showed a gradual resolution of the signs of NEC.

On the 15th day of life intestinal feeding was begun, but at a very slow rate. Over the next week L-2-oxothiazolidine-4-carboxylate was infused via the parenteral nutrition solution, although the proportion of nutrients derived from this source was gradually decreased in favor of enteral feeding.

On day 22 of life enteral feeding comprised 75-80% of needs, with the rest being parenteral. Since signs of intestinal problems had disappeared, the L-2-oxothiazolidine-4-carboxylate dosing was ended. The infant recovered well and was discharged 38 days after birth.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim as our invention:

1. A method for treating reperfusion injury comprising the step of administering to a patient in danger of a reperfusion injury a therapeutically effective amount of a composition comprising L-2-oxothiazolidine-4-carboxylic acid.

2. The method of claim 1 wherein the L-2-oxothiazolidine-4-carboxylic acid is administered at a dose ranging from approximately 5 mg/kg body weight/day to about 500 mg/kg body weight/day.

3. The method of claim 1 wherein the method includes also administering a therapeutically effective amount of an amino acid solution including: arginine; leucine; isoleucine; lysine; valine; phenylalanine; histidine; threonine; methionine; tryptophan; alanine; proline; serine; tyrosine; and amino-acetic acid.

4. The method of claim 3 wherein the L-2-oxothiazolidine-4-carboxylic acid is administered at a dose of approximately 5 to about 500 mg/kg/day.

5. The method of claim 3 wherein the L-2-oxothiazolidine-4-carboxylic acid and amino acids are administered enterally.

6. The method of claim 3 wherein the L-2-oxothiazolidine-4-carboxylic acid and amino acids are administered parenterally.

7. The method of claim 1 wherein the L-2-oxothiazolidine-4-carboxylic acid composition is administered with additional glutathione esters.

8. The method of claims 7 wherein the esters include a methyl ester.

9. The method of claim 7 wherein the esters include an ethyl ester.

10. The method of claim 7 wherein the esters include an isopropyl ester.

11. The method of claim 1 wherein glutathione esters are additionally administered during the treatment.

12. The method of claim 1 wherein the L-2-oxothiazolidine-4-carboxylic acid is administered enterally.

13. The method of claim 1 wherein the L-2-oxothiazolidine-4-carboxylic acid is administered parenterally.

14. A method for limiting an ischemic reperfusion injury comprising the step of administering prior to an expected ischemic event a therapeutically effective amount of a composition comprising L-2-oxothiazolidine-4-carboxylate.

15. The method of claim 14 which additionally includes the administration of a therapeutically effective amount of an amino acid solution including: arginine; leucine; isoleucine; lysine; valine; phenylalanine; histidine; threonine; methionine; tryptophan; alanine; proline; serine; tyrosine; and amino-acetic acid.

16. The method of claim 14 wherein the treatment includes additional administration of glutathione esters.

17. The method of claim 16 wherein the esters include a methyl ester.

18. The method of claim 16 wherein the esters include an ethyl ester.

19. The method of claim 16 wherein the esters include an isopropyl ester.

20. The method of claim 14 wherein the composition is administered prior to angioplasty.

21. The method of claim 14 wherein the composition is administered prior to coronary bypass surgery.

22. The method of claim 14 wherein the composition is administered enternally.

23. The method of claim 14 wherein the composition is administered parenterally.

24. A method for limiting ischemic reperfusion injury comprising the step of administering to a patient after the onset of an ischemic event a therapeutically effective amount of a composition comprising L-2-oxothiazolidine-4-carboxylate.

25. The method of claim 24 which additionally includes the administration of a therapeutically effective amount of an amino acid solution including: arginine; leucine; isoleucine; lysine; valine; phenylalanine; histidine; threonine; methionine; tryptophan; alanine; proline; serine; tyrosine; and amino-acetic acid.

26. The method of claim 24 wherein the treatment includes additional administration of glutathione esters.

27. The method of claim 26 wherein the esters include a methyl ester.

28. The method of claim 26 wherein the esters include an ethyl ester.

29. The method of claim 26 wherein the esters include an isopropyl ester.

30. The method of claim 24 wherein the composition is administered parenterally.

31. The method of claim 24 wherein the composition is administered enterally.

32. The method of claim 24 wherein approximately 5 mg/kg body weight/day to about 500 mg/kg body weight/day L-2-oxothiazolidine-4-carboxylate is administered to the patient.

33. A method for treating a cardiac ischemic event comprising the step of administering to a patient after the onset of the ischemic event a therapeutically effective amount of a composition comprising L-2-oxothiazolidine-4-carboxylate.

34. The method of claim 33 wherein the treatment includes additional administration of a therapeutically effective amount of an amino acid solution including: arginine; leucine; isoleucine; lysine; valine; phenylalanine; histidine; threonine; methionine; tryptophan; alanine; proline; serine; tyrosine; and amino-acetic acid.

35. The method of claim 33 wherein the treatment includes the additional administration of glutathione esters.

36. A method for treating an intestinal ischemic event comprising the step of administering to a patient after the onset of the ischemic event a therapeutically effective amount of a composition comprising L-2-oxothiazolidine-4-carboxylate.

37. The method of claim 36 wherein the method includes also administering a therapeutically effective amount of an amino acid solution including: arginine; leucine; isoleucine; lysine; valine; phenylalanine; histidine; threonine; methionine; tryptophan; alanine; proline; serine; tyrosine; and amino-acetic acid.

38. The method of claim 36 wherein the treatment includes the additional administration of glutathione esters.

39. A method for treating a cerebral ischemic event comprising the steps of administering to a patient after the onset of the ischemic event a therapeutically effective amount of L-2-oxothiazolidine-4-carboxylate.

40. The method of claim 39 wherein the method includes also administering a therapeutically effective amount of an amino acid solution including: arginine; leucine; isoleucine; lysine; valine; phenylalanine; histidine; threonine; methionine; tryptophan; alanine; proline; serine; tyrosine; and amino-acetic acid.

* * * * *